United States Patent

Knopf et al.

[11] Patent Number: 5,919,233
[45] Date of Patent: *Jul. 6, 1999

[54] FLEXIBLE IMPLANT

[75] Inventors: Wieland Knopf, Georgenthal; Susanne Landgrebe, Norderstdt, both of Germany

[73] Assignee: Ethicon, Inc., Somerville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/882,063

[22] Filed: Jun. 25, 1997

Related U.S. Application Data

[63] Continuation of application No. 08/567,826, Mar. 6, 1996, abandoned, which is a continuation of application No. 08/239,622, May 9, 1994, abandoned.

[30] Foreign Application Priority Data

May 12, 1993 [DE] Germany .............................. 43 16 673

[51] Int. Cl.⁶ ...................................................... A61F 2/02
[52] U.S. Cl. .............................. 623/11; 623/13; 606/157; 606/158; 600/37
[58] Field of Search ........................ 623/11, 13; 606/157, 606/158; 600/37

[56] References Cited

U.S. PATENT DOCUMENTS

| 3,875,928 | 4/1975 | Angelchik | 623/66 |
| 4,069,825 | 1/1978 | Akiyama | 606/158 |
| 4,271,828 | 6/1981 | Angelchik | 128/898 |
| 4,796,603 | 1/1989 | Dahlke et al. | 623/11 |
| 5,171,253 | 12/1992 | Klieman | 606/158 |
| 5,197,983 | 3/1993 | Berman et al. . | |
| 5,356,431 | 10/1994 | Pierce | 623/11 |
| 5,540,703 | 7/1996 | Borker, Jr. et al. | 623/13 |

FOREIGN PATENT DOCUMENTS

| 0 238 219 A1 | 9/1987 | European Pat. Off. . |
| 0 485 047 A1 | 5/1992 | European Pat. Off. . |
| 3619197 A1 | 12/1987 | Germany . |

*Primary Examiner*—Paul B. Prebilic
*Attorney, Agent, or Firm*—Emil Richard Skula

[57] ABSTRACT

A flexible implant (1) with a cylinder-like basic form has near its first end (2) an eye-like opening (3), the axis (4) of which runs transversely to the cylinder axis. The implant (1) can be closed to a ring form by guiding the second end (6) through the opening (3), and is thus suitable in particular for the treatment of reflux oesophagitis and/or axial hiatus hernia.

4 Claims, 2 Drawing Sheets

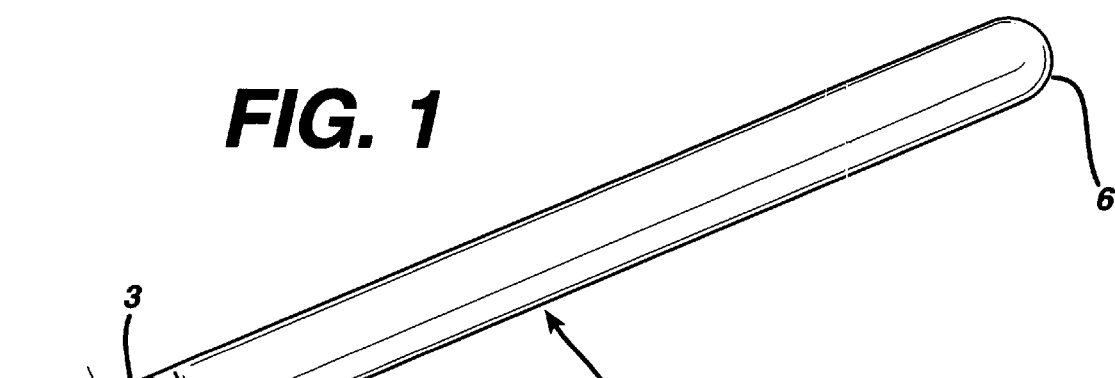
FIG. 1
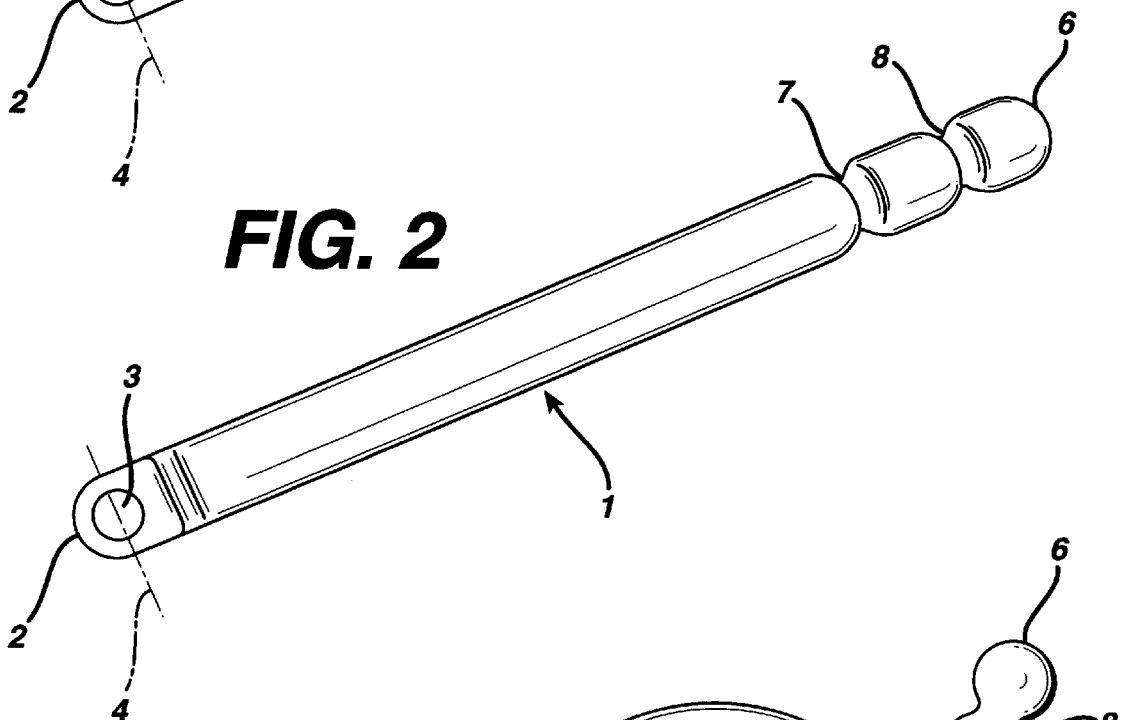
FIG. 2
FIG. 3

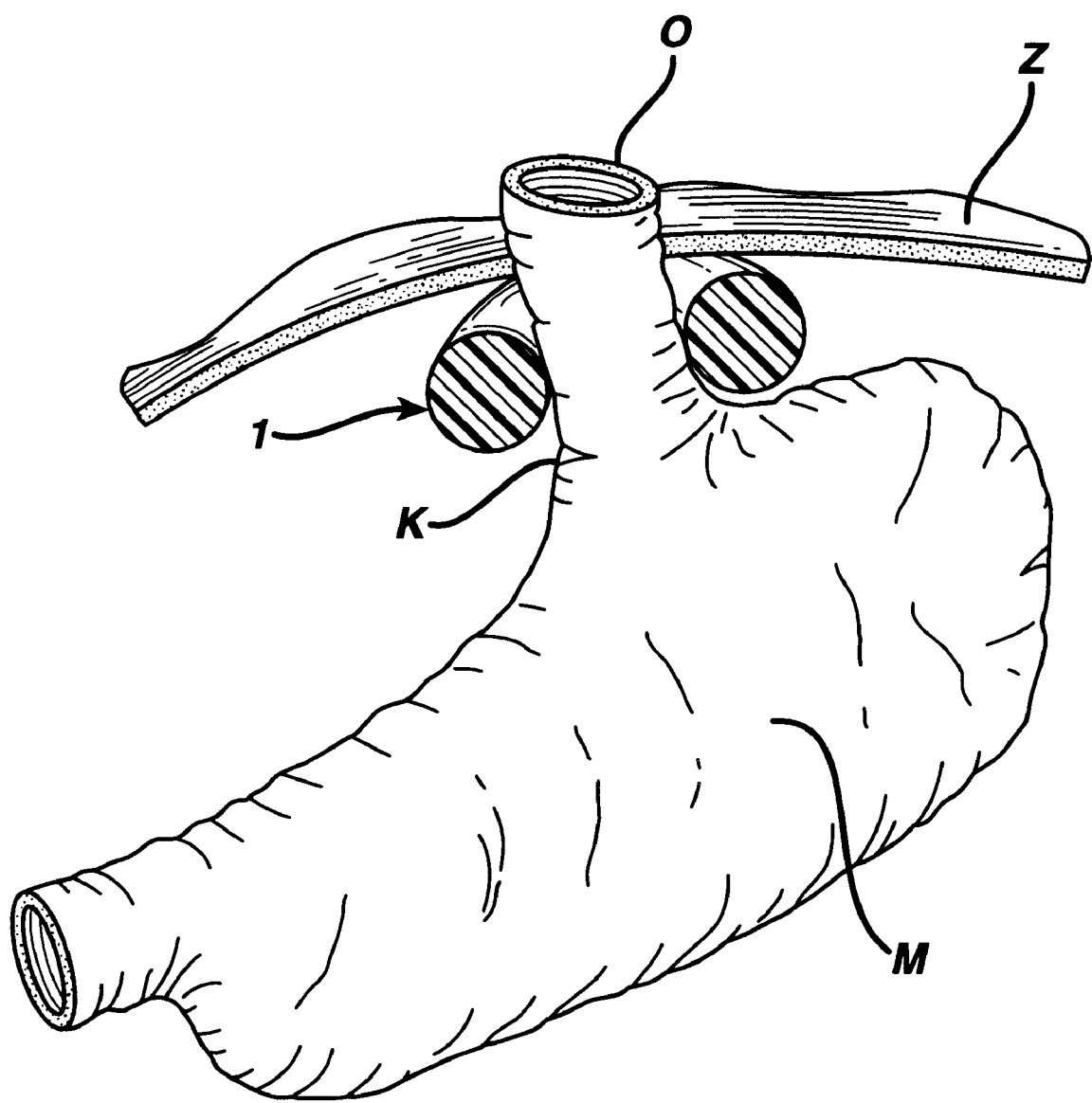

FLEXIBLE IMPLANT

This application is a continuation of application Ser. No. 08/567,826 filed Mar. 6, 1996 and now abandoned which is a continuation of application Ser. No. 08/239,622 filed May 9, 1994 and now abandoned, which is hereby incorporated by reference.

FIELD OF THE INVENTION

The invention relates to a flexible implant, in particular for the treatment of reflux oesophagitis and/or axial hiatus hernia.

BACKGROUND OF THE INVENTION

Described in European Patent No. 0 061 540 is a prosthesis also known under the name ANGELCHIK anti-reflux prosthesis which is used for the treatment of reflux oesophagitis. It is essentially a C-shaped cushion element, preferably of silicon, at the two ends of which is attached a flexible strip in each case. In a surgical operation this prosthesis is placed around the distal region of the gullet (oesophagus), above the cardiac orifice (cardia) and below the midriff (diaphragm). When the C-shaped part encloses the oesophagus, the two flexible strips are knotted together. In this way a ring forms which prevents a rising of stomach parts into the thorax area in the case of an axial hiatus hernia, and simultaneously reduces a reflux of the stomach contents into the distal area of the oesophagus.

The previously-known anti-reflux prosthesis cannot be inserted into the abdominal cavity via a cannula (trocar sleeve); a laparotomy is required for this. Only the positioning and the knotting of the two flexible strips are possible endoscopically, something which does, however, require much skill from the operator.

SUMMARY OF INVENTION

It is the object of the invention to provide an implant, particularly for the treatment of reflux oesophagitis and/or axial hiatus hernia, which can be inserted into the body cavity via a cannula in an endoscopic operation.

This object is achieved by a flexible implant with a cylinder-like basic form, the implant having, near its first end, an eye-like opening, the axis of which runs transversely to the cylinder axis.

The basic form of the implant according to the invention is not C-shaped or ring-shaped, but cylinder-like. In order that the implant can be placed beneath the diaphragm around the oesophagus, it is of flexible design. Near one of its ends, the cylinder-like basic form has an eye-like opening, the axis of which runs transversely to the cylinder axis. After the implant has been placed to produce an annular shape, the other end can be pushed through this eye-like opening, thus closing the ring permanently. The size of the eye-like opening is selected so that frictional forces effectively prevent an opening of the ring once it is joined.

The implant is preferably designed flat in the area of the eye-like opening. In the area of its second end, the implant can be provided with one or more constrictions, offset against each other along the length of the cylinder axis. When, after the implant has been brought into the form of a ring, such a constriction comes to lie in the area of the eye-like opening, the final form of the implant is particularly securely fixed. If several constrictions are provided, the diameter of the ring form can be varied.

As the implant according to the invention is cylinder-like in its basic form, i.e. elongated, it can be introduced into the inside of the body without difficulties through a conventional cannula, as is used in endoscopic operations. If the implant is to be used as an anti-reflux prosthesis, it can be gripped without particular difficulty by endoscopic gripping instruments, which are introduced into the abdominal region through further cannulae, and placed around the oesophagus in the form of a ring. The second end of the implant is then pulled through the eye-like opening using these gripping instruments and the ring closed until the desired size is achieved. Complicated knotting of the two ends of the implant is therefore not required. Insertion is carried out quickly and safely, and all the advantages which the endoscopic operation technique offers are enjoyed.

In an advantageous embodiment, the flexible implant according to the invention is partially or completely produced from a resorbable material. Such an implant can promote tissue formation selectively, in that cells can grow into the material and thus form new tissue before the material is resorbed. In this way, the new tissue takes over the original function of the implant, namely a supportive mechanical action. On the other hand, the disadvantages which substances alien to the body, e.g. silicon, can cause in the long term, do not apply.

The invention is explained in the following with reference to embodiments.

BRIEF DESCRIPTION OF THE DRAWINGS

FIG. 1 is a first version of the implant according to the invention in its cylinder-like basic form;

FIG. 2 is a second version of the implant according to the invention in its cylinder-like basic form;

FIG. 3 is a top view of the second version of the implant according to the invention, after it has been closed to a ring form; and FIG. 4 is a diagrammatic representation of the use of the implant according to the invention with a hiatus hernia, a part of the ring form being removed for clarification.

DESCRIPTION OF PREFERRED EMBODIMENTS

FIG. 1 shows an implant 1 before it is made into a ring form. The basic form of the implant is cylinder-like. Near to its first end 2 the implant 1 has a continuous opening 3, the axis 4 of which runs transversely to the cylinder axis (not shown). The axis 4 can extend at a right angle or at another angle, i.e. obliquely, relative to the cylinder axis. The implant 1 is preferably designed flat in the area of the opening 3, as can be seen from the view represented in FIG. 3. The implant 1 can be rounded both at its first end 2 and at its second end 6. The size of the opening 3 is somewhat smaller than the crosssectional area of the implant 1. Since the implant 1 consists of a flexible material, the opening 3 yields slightly on introducing the second end 6, with the result that the second end 6 can be pushed through and then held securely by frictional forces.

With the version shown in FIG. 2, the implant 1 is provided in the area of its second end 6 with two constrictions 7 and 8 which are offset against each other along the axis of the cylinder. The cross-sectional area at the constrictions 7 and 8 is approximately as large as that of the opening 3. If the implant 1 is closed to a ring form, see FIG. 3, a particularly stable fixing is achieved, whenever the eye-shaped opening 3 comes to rest in the region of a constriction 7 or 8. In order to achieve the position shown in FIG. 3, the area of the constriction 8 was pulled completely through the opening 3, with the result that the opening 3 now lies in the area of the constriction 7, thus giving rise to a narrower ring form.

The implant according to the invention consists of any flexible material which is tissue-compatible and can be used for the intended medical purpose. If the implant 1 or a part of it consists of a resorbable material, polydioxanone, polyglactin or a mixture of them can, for example, be used for this purpose.

FIG. 4 illustrates how the oesophagus O travels through the diaphragm Z and opens out into the stomach M at the cardia K.

For the treatment of reflux oesophagitis and/or axial hiatus hernia, an implant 1 according to the invention is placed as a ring around the oesophagus 0 below the diaphragm Z and above the cardia K.

The implant according to the invention is not limited to use in endoscopic operations, but can also be used advantageously in open surgery.

We claim:

1. A method of medically treating an axial hiatus hernia, comprising
   A) placing a flexible implant around the oesophagus below the diaphragm, wherein the flexible insert comprises:
      a flexible, cylindrical member, said member having a first end and an opposed second end, said member having a longitudinal axis;
      a flat tab member extending from the first end;
      a rounded tip extending from the second end;
      a hole in said flat tab member, said hole having an outer periphery;
      at least one circular groove in the second end of the cylindrical member, such that when said second end is inserted into the hole of the tab member, at least one groove is engaged by the outer periphery of the hole thereby locking the second end to the tab member; and,
   B) locking the implant in place about the oesophagus.

2. The method of claim 1 wherein the implant further comprises a bioabsorbable material.

3. A method of medically treating reflex oesophagitis comprising:
   A) placing a flexible implant around the oesophagus below the diaphragm wherein the flexible insert comprises:
      a flexible, cylindrical member, said member having a first end and an opposed second end, said member having a longitudinal axis;
      a flat tab member extending from the first end;
      a rounded tip extending from the second end;
      a hole in said flat tab member, said hole having an outer periphery;
      at least one circular groove in the second end of the cylindrical member, such that when said second end is inserted into the hole of the tab member, at least one groove is engaged by the outer periphery of the hole thereby locking the second end to the tab member; and,
   B) locking the implant in place about the esophagus.

4. The method of claim 3 wherein the implant further comprises a bioabsorbable material.

* * * * *